United States Patent [19]

Varma et al.

[11] Patent Number: 4,654,364
[45] Date of Patent: Mar. 31, 1987

[54] HYDROXAMIC ACIDS OF 7-OXABICYCLOHEPTANE SUBSTITUTED ETHERS

[75] Inventors: Ravi K. Varma, Belle Mead; Jagabandhu Das, Plainsboro, both of N.J.

[73] Assignee: E. R. Squibb & Sons, Inc., Princeton, N.J.

[21] Appl. No.: 797,300

[22] Filed: Nov. 12, 1985

Related U.S. Application Data

[63] Continuation-in-part of Ser. No. 677,131, Nov. 30, 1984.

[51] Int. Cl.[4] .................... C07D 493/08; A61K 31/34
[52] U.S. Cl. .................................... 514/469; 549/463
[58] Field of Search ...................... 548/252; 549/463; 514/469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,474,803 | 10/1984 | Hall | 514/469 |
| 4,536,513 | 8/1985 | Das et al. | 514/469 |
| 4,582,854 | 4/1986 | Hall | 514/469 |

FOREIGN PATENT DOCUMENTS 0043292 8/1982 European Pat. Off.
2039909 8/1980 United Kingdom.

Primary Examiner—Robert Gerstl
Attorney, Agent, or Firm—Lawrence S. Levinson; Burton Rodney

[57] ABSTRACT

Hydroxamic acids of 7-oxabicycloheptane substituted ether prostaglandin analogs are provided having the structural formula

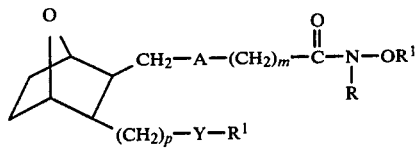

wherein Y is O or

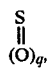

and including all stereoisomers thereof.

The compounds are inhibitors of $\Delta^5$-lipoxygenase and inhibitors of prostaglandin and leukotriene biosynthesis and as such are useful, for example, as anti-allergy and antiinflammatory agents and also as antipsoriatic agents.

16 Claims, No Drawings

HYDROXAMIC ACIDS OF 7-OXABICYCLOHEPTANE SUBSTITUTED ETHERS

REFERENCE TO OTHER APPLICATIONS

This application is a continuation-in-part of application Ser. No. 677,131, filed Nov. 30, 1984.

DESCRIPTION OF THE INVENTION

The present invention relates to hydroxamic acids of 7-oxabicycloheptane substituted ethers which are inhibitors of $\Delta^5$-lipoxygenase and inhibitors of prostaglandin and leukotriene biosynthesis and as such are useful, for example, as anti-allergy and antiinflammatory and also as antisporiatic agents. These compounds have the structural formula

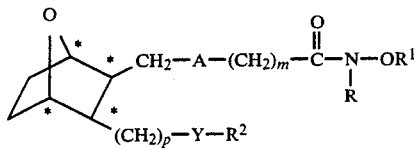

and including all stereoisomers thereof, wherein A is —CH=CH— or —(CH$_2$)$_2$; m is 1 to 10; R is H or lower alkyl; R$^1$ is H, lower alkyl, aryl, aralkyl, cycloalkyl, alkanoyl or aroyl; p is 1 to 5; Y is O or S(O)$_q$ wherein q is 0, 1 or 2; and R$^2$ is lower alkyl, aryl, aralkyl, cycloalkyl, cycloalkylalkyl, lower alkenyl or lower alkynyl, provided that when R$^1$ is H, Y is S(O)$_q$.

Thus, the compounds of the invention include the following types of compounds:

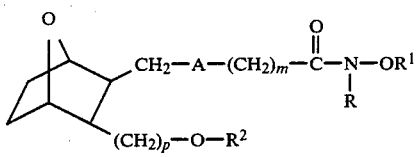

IA

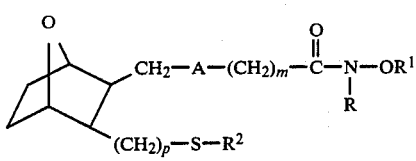

IB

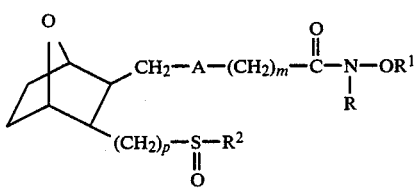

IC

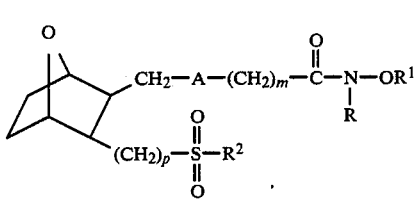

ID

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), lower alkoxy groups and/or 1 or 2 hydroxyls.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms "alkanoyl" and "aroyl" refer to a lower alkyl group linked to a carbonyl group or an aryl group linked to a carbonyl group.

The term "halogen" or "halo" as used herein by itself or as part of another group refers to chlorine, bromine, fluorine or iodine, with chlorine being preferred.

The terms "(CH$_2$)$_m$" and "(CH$_2$)$_p$" include a straight or branched chain radical having 1 to 10 carbons in the normal chain in the case of "(CH$_2$)$_m$" and 1 to 5 carbons in the normal chain in the case of "(CH$_2$)$_p$" and may contain one or more lower alkyl and/or halogen substituents. Examples of (CH$_2$)$_m$ and (CH$_2$)$_p$ groups include

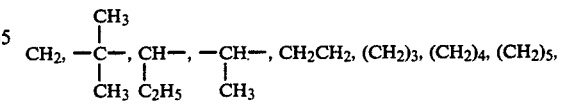

-continued $(CH_2)_6$, $(CH_2)_7$, $(CH_2)_8$, $(CH_2)_9$, $(CH_2)_{10}$, $-CH_2-CH_2-\underset{CH_3}{\overset{CH_3}{C}}-$, $-\underset{CH_3}{\overset{CH_3}{C}}-CH_2-$, $-(CH_2)_2-\underset{}{\overset{CH_3}{CH}}-$, $-CH_2-\underset{}{\overset{CH_3}{CH}}-$, $-(CH_2)_2-\underset{CH_3}{\overset{CH_3}{C}}-$, $-CH_2-\underset{CH_3}{\overset{}{CH}}-\underset{CH_3}{\overset{}{CH}}-CH_2-$, $-CH_2-\underset{CH_3}{\overset{}{CH}}-CH_2-\underset{CH_3}{\overset{}{CH}}-$ and the like.

Preferred are those compounds of formula I wherein A is $-CH=CH-$ or $-CH_2-CH_2-$, m is 1 to 3, p is 1, Y is O or S, R is alkyl, $R^1$ is H and $R^2$ is lower alkyl, such as hexyl, aryl, such as phenyl, or aralkyl such as benzyl.

The various compounds of the invention may be prepared as outlined below.

The 7-oxabicycloheptane ether compounds of formula I of the invention wherein Y is O, p is 1, A is $CH=CH$ or $CH_2-CH_2$, and m is 0 to 10, that is,

[Structure IE: bicyclic with $CH_2-A-(CH_2)_m-\overset{O}{\overset{\|}{C}}-\underset{R}{N}-OR^1$ and $CH_2-O-R^2$]

may be prepared starting with the alcohol II

[Structure II: bicyclic with $CH_2-A-(CH_2)_m-CO_2$alkyl and $CH_2OH$]

which is subjected to an ether formation reaction wherein compound II is reacted with a strong base such as KOH, NaOH or LiOH and the like in the presence of an inert solvent, such as xylene, toluene, benzene or mesitylene and sulfonate compound of the structure Mesyl-$OR^2$  A or Tosyl-$OR^2$  A' or a halide of the structure $R^2$ Hal (Hal is Cl, Br or I)  A"

to form the ether

[Structure III: bicyclic with $CH_2-CH=CH-(CH_2)_m-COO$alkyl and $CH_2-O-R^2$]

Ether III is then hydrolyzed by treating with strong base such as LiOH, KOH or NaOH to form the corresponding alkali metal salt and then neutralizing with a strong acid such as HCl or oxalic acid to form IV

[Structure IV: bicyclic with $CH_2-CH=CH-(CH_2)_m-CO_2H$ and $CH_2-O-R^2$]

Acid IV is then subjected to hydroxamate formation by treating a solution of IV in an inert aromatic solvent such as benzene with oxalyl chloride and stirring the mixture at room temperature under nitrogen to form the acid chloride V

[Structure V: bicyclic with $CH_2-CH=CH-(CH_2)_m-COCl$ and $CH_2-O-R^2$]

The acid chloride V is dissolved in an inert solvent such as tetrahydrofuran and added to a cold solution of VA $\underset{R}{\overset{HNOR^1}{|}}$  VA in tetrahydrofuran and water in the presence of organic base such as triethylamine. The mixture is stirred under nitrogen atmosphere while being cooled in an ice bath, to form hydroxamate IE.

Compounds of the invention wherein p is 1, Y is O, A is $CH_2-CH_2$ and m is 0 to 10 may be prepared by subjecting acid IV to hydrogenation by treating IV with hydrogen in the presence of a catalyst such as palladium and solvent such as methanol to form acid VI

[Structure VI: bicyclic with $CH_2-(CH_2)_2-(CH_2)_m-CO_2H$ and $CH_2-O-R^2$]

which is then converted to the corresponding hydroxamate IF as described above with respect to the conversion of acid IV to the hydroxamate IF

[Structure IF: bicyclic with $CH_2-(CH_2)_2-(CH_2)_m-\overset{O}{\overset{\|}{C}}-\underset{R}{N}-OR^1$ and $CH_2-O-R^2$]

Compounds of formula I wherein Y is S, A is $CH=CH$ and p is 1, or Y is O or S, $R^2$ is benzyl, A is $CH=CH$ or $(CH_2)_2$ and p is 1, may be prepared by starting with the hydroxymethyl compound IIA

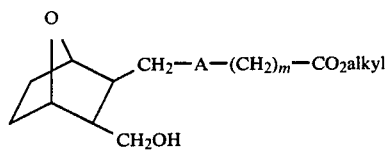
IIA and subjecting IIA to a tosylation reaction, for example, by reacting the hydroxymethyl compound IIA with tosyl chloride in pyridine and methylene chloride to form the corresponding tosylate VII

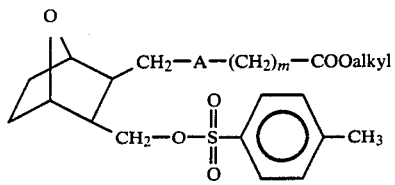
VII

Thereafter, tosylate VII is reacted with a thiol or mercaptan of the structure B $$HSR^2 \qquad (B)$$

in the presence of potassium t-butoxide and a solvent such as tetrahydrofuran, dimethyl sulfoxide or dimethylformamide to form compounds of the invention of the structure VIII

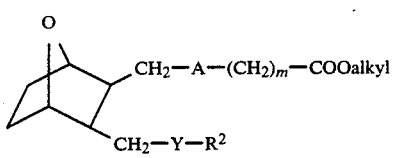
VIII

Ester VIII may then be hydrolyzed by treating with strong alkali metal base under an oxygen-free atmosphere in the presence of anti-oxidants like hydroquinone and then neutralizing with a strong acid, as described hereinbefore, to form the acid IX

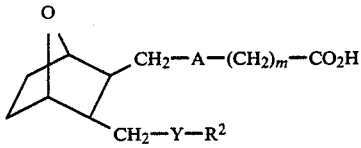
IX

Compound IX is then subjected to hydroxamate formation as described hereinbefore to form the hydroxamate IG of the invention

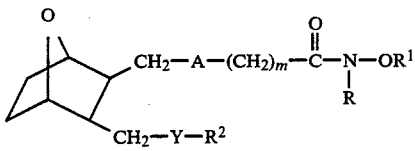
IG

Compounds of the invention wherein p is 1, Y is S, A is $CH_2$—$CH_2$ and m is 0 to 6 may be prepared by subjecting the hydroxymethyl compound II to hydrogenation by treating IIA with hydrogen in the presence of a catalyst such as palladium and a solvent such as methanol to form hydroxymethyl compound IIB

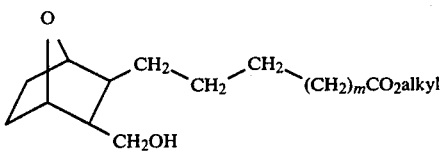
IIB

Compound IIB is then subjected to a tosylation reaction, for example, by reacting the hydroxymethyl compound with tosyl chloride in pyridine and methylene chloride to form the corresponding tosylate IIIA

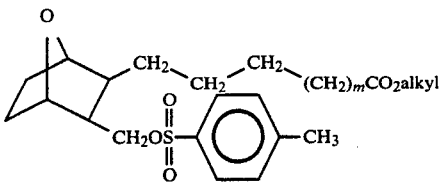
IIIA

Thereafter, tosylate IIIA is reacted with a thiol or mercaptan of the structure B, above, in the presence of potassium t-butoxide and a solvent, such as tetrahydrofuran, dimethylsulfoxide, or dimethylformamide to form compounds of the invention of structure X

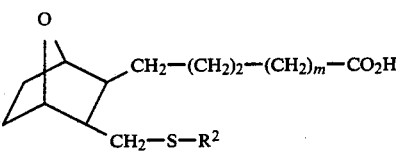
X

Compound X is then subjected to hydroxamate formation as described hereinbefore to form hydroxamate IH of the invention

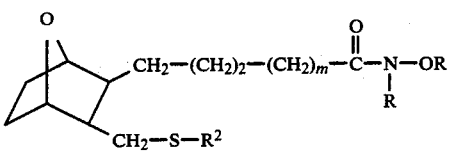
IH

Compounds of formula I wherein p is 2 to 5 may be prepared by subjecting hydroxymethyl compound IIA (wherein A is CH=CH) or hydroxymethyl compound IIB (wherein A is —$(CH_2)_2$—) (formed by reducing IIA by treating with hydrogen in the presence of a palladium on carbon catalyst) to a Collins oxidation by reacting IIA or IIB with chromium trioxide-pyridine complex in the presence of a solvent such as dichloromethane to form aldehyde XI. Aldehyde XI

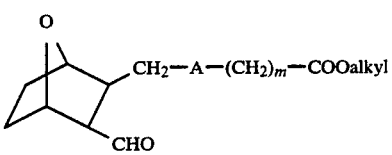
XI wherein A is CH=CH or $CH_2$—$CH_2$ is subjected to a homologation sequence, such as a Wittig reaction with $(C_6H_5)_3P^+Cl^-CH_2OCH_3$ followed by hydrolysis, (p−1) times, to form aldehyde XII

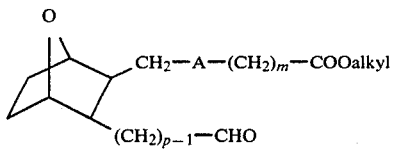

XII which is carried on to compounds of the invention where p is 2 to 5 by reducing aldehyde XII employing a reducing agent such as sodium borohydride in a solvent such as methanol to form alcohol ester XIII

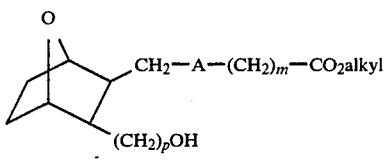

XIII which is subjected to an etherification reaction with A, A' or A" as described above or to a thioetherification reaction with thiol B after conversion of XIII to its tosylate to form XIV

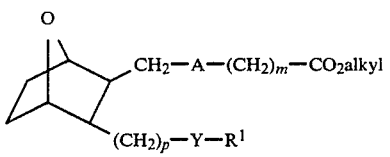

XIV

Compound XIV is then subjected to hydroxamate formation as described hereinbefore to form hydroxamate IJ of the invention

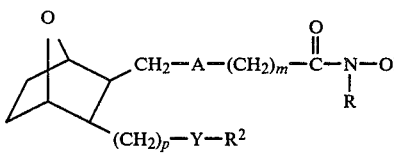

IJ wherein A is CH=CH or $(CH_2)_2$, p is 2 to 5 and Y is O or S

To form compounds of formula I wherein Y is

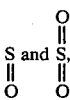

the sulfide derivative of formula I wherein Y is S is subjected to an oxidation reaction, for example, by reacting same with sodium periodate, in the presence of methanol and tetrahydrofuran and water, to form the corresponding sulfinyl derivative

and sulfonyl derivative

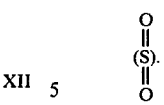

The sulfinyl and sulfonyl derivatives may be separated by chromatography or other conventional separation procedures.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

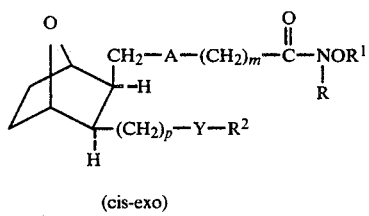

Ia (cis-exo)

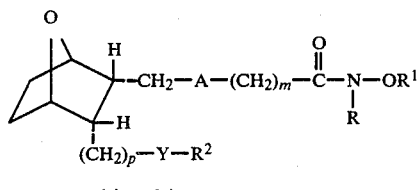

Ib (cis-endo)

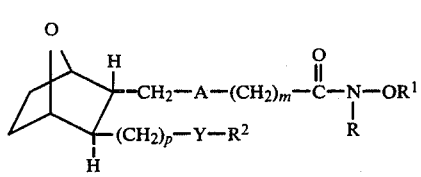

Ic (trans)

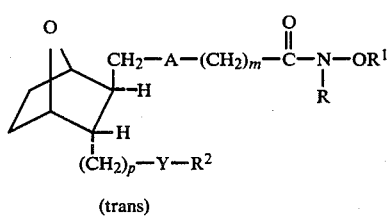

Id (trans)

The nucleus in each of the compounds of the invention is depicted as

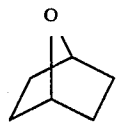

for matter of convenience; it will also be appreciated that the nucleus in the compounds of the invention may be depicted as

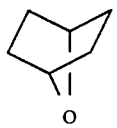

The compounds of this invention are cardiovascular agents useful as platelet aggregation inhibitors, such as inhibiting arachidonic acid-induced platelet aggregation (e.g., for treatment of thrombotic disease, such as inhibiting coronary or cerebral thromboses) and in inhibiting bronchoconstriction as induced by asthma. They are also selective thromboxane $A_2$ receptor antagonists, e.g., having a vasodilatory effect for treatment of myocardial ischemic disease, such as angina pectoris.

The compounds of the invention are also thromboxane synthetase inhibitors and thus may also be used for preventing gastrointestinal ulcer formation. They also increase the amount of endogenous prostacyclin $PGD_2$ and therefore may be used for controlling tumor cell metastasis or as antihypertensive agents.

The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of this invention may also be used in combination with a cyclic AMP phosphodiesterase (PDE) inhibitor such as theophylline or papaverine in the preparation and storage of platelet concentrates.

In addition, the compounds of the invention are $\Delta^5$-lipoxygenase inhibitors and prevent prostaglandin and leukotriene $C_4$ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma. In addition, the compounds of the invention are useful as antipsoriatic agents.

The compounds of the invention as well as the acid precursors thereof are useful as antiinflammatory agents in the manner of indomethacin and phenylbutazone as indicated by carragenin-induced edema in the rat [Ref: Winter et al, J. Pharmacol, Exp. Ther. 141:369, 1963] and they may be used to decrease joint swelling, tenderness, pain and stiffness in conditions such as rheumatoid arthritis.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1R-[1α,2β(5Z),3β,4α]]-7-[3-[(Hexyloxy)methyl]-7-oxabicyclo[2.2.1]hept-2-yl]-N-hydroxy-N,2,2-trimethyl-5-heptenamide

A.

[3aR-[1-(1R,2S,5R),3aα,4α,7α,7aα]]-Octahydro-1-[[5-methyl-2-(1-methylethyl)cyclohexyl]oxy]-4,7-epoxyisobenzofuran A solution of (exo)-octahydro-4,7-epoxyisobenzofuran-1-ol prepared as described in U.S. Pat. No, 4,143,054 (21 g, 0.13 mole), levo-menthol (21 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S,5R),3aα,4α,7α,7aα]]-octahydro-1-[[5-methyl-2-(1-methylethyl)cyclohexyl]oxy]-4,7-epoxyisobenzofuran, m.p. 109°–111° C.

B.

[3aS-(3aα,4α,7α,7aα)]-Octahydro-1-benzyloxy-4,7-epoxyisobenzofuran

A solution of [3aR-[1-(1R,2S,5R),3aα,4α,7α,7aα]]-octahydro-1-[[5-methyl-2-(1-methylethyl)cyclohexyl]oxy]-4,7-epoxy-isobenzofuran (from Part A) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1), $R_f$=0.25; vanillin spray and heat.

C.

[3aS-(3aα,4α,7α,7aα)]-Octahydro-4,7-epoxyisobenzofuran-1-ol

A mixture of title B compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C. $[\alpha]_D = -44°$ $[\alpha]^{Hg}{}_{365} = -122°$ c=10 mg/ml MeOH.

TLC: silica gel; ethyl acetate/dichloromethane (1:1), $R_f = 0.2$; vanillin spray and heat.

D.
[1R-(1α,2β,3β,4α)]-3-(Hydroxymethyl)-2-(2-methoxyethenyl)-7-oxabicyclo[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane] in tetrahydrofuran (20 ml). The mixture was stirred at room temperature for 30 minutes then treated with title C compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title B product contaminated with phosphine oxide. This product was distilled in vacuo to yield 3 g of title D compound, b.p. 90° C./0.01 mm.

$[\alpha]_D = +44°$ $[\alpha]^{Hg}{}_{365} = +138°$ c=11 mg/ml MeOH.

TLC: silica gel; ethyl acetate/dichloromethane (1:1); $R_f = 0.2$; vanillin spray and heat.

E.
[4aS-(4aα,5α,8α,8aα)]-Octahydro-5,8-epoxy-(1H)-benzopyran-3-ol

A solution of title D compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title E compound, m.p. 104°–105° C.

$[\alpha]_D = +27.2°$ $[\alpha]^{Hg}{}_{365} = 0°$, (c=7.9 mg/ml MeOH).

F.
[1R-[1α,2β(5Z),3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title E compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D = +11.2°$ $[\alpha]^{Hg}{}_{365} = 0°$, (c=16.9 mg/ml MeOH).

TLC: silica gel; ether; $R_f = 0.4$; vanillin spray and heat.

G.
[1R-[1α,2β(5Z),3β,4α]]-7-[3-[(Hexyloxy)methyl]-7-oxabicyclo[2.2.1]hept-2-yl]-5-heptenoic acid, hexyl ester A mixture of powdered KOH (0.93 g) in 25 ml of dry xylene was heated to reflux under argon atmosphere and 12 ml of xylene was removed by distillation. To this mixture was added simultaneously a solution of 500 mg (1.86 mmol) of title F alcohol methyl ester in 16 ml of dry xylene and a solution of 1.68 g (9.30 mmol) hexylmesylate in 16 ml of dry xylene. This mixture containing a jelly-like solid was refluxed for 1 hour and 15 minutes. The cooled reaction mixture was diluted with 100 ml of saturated NaHCO₃ solution and extracted with CH₂Cl₂ (3×100 ml). The combined CH₂Cl₂ extracts were washed with brine (1×200 ml), dried (MgSO₄), filtered and concentrated in vacuo. Purification was effected by flash chromatography on 46 g of silica gel 60 using hexane:ethane (5:1) as eluant. This gave 0.62 g of title hexyl ester (79%) as a colorless oil.

TLC: silica gel, 2% $CH_3OH/CH_2Cl_2$, $R_f$ 0.80, iodine.

H.
1R-[1α,2β(5Z),3β,4α]]-7-[3-[(Hexyloxy)methyl]-7-oxabicyclo[2.2.1]hept-2-yl]-5-heptenoic acid To a stirred solution of 517 mg (1.12 mmol) of Part G hexyl ester, 55 ml of distilled THF, 4.40 ml of $CH_3OH$ and 7.20 ml of $H_2O$ under argon was added 13.50 ml of 1N aqueous lithium hydroxide solution. This mixture was purged with argon vigorously for 30 minutes and stirred at room temperature for 15 hours. The reaction mixture was acidified to pH 3 by the addition of 1N aqueous HCl solution. The resulting solution was poured into 120 ml of saturated NaCl solution and was saturated with solid NaCl. The aqueous layer was extracted with EtOAc (4×150 ml). The combined EtOAc extracts were dried (MgSO₄), filtered and concentrated in vacuo. This was chromatographed on 40 g of silica gel 60 using Et₂O:hexane (1:4, 1:1) and Et₂O as eluant to give the desired product contaminated with a small amount of hexyl alcohol. The product was pumped under high vacuum for ~60 hours at room temperature to give 350 mg (85%) of pure title acid. TLC:silica gel, 4% $CH_3OH/CH_2Cl_2$, $R_f=0.42$, iodine.

$[\alpha]_D = +5.2°$ (CHCl$_3$).

Anal Calcd for $C_{20}H_{34}O_4$: C, 70.92; H, 10.12. Found: C, 70.66; H, 9.99.

I.
[1R-[1α,2β(5Z),3β,4α]]-7-[3-[(Hexyloxy)methyl]-7-oxabicyclo[2.2.1]hept-2-yl]-5-heptenoic acid, methyl ester

[1R-[1α,2β(Z),3β,4α]]-7-[3-[(Hexyloxy)methyl]-7-oxabicyclo[2.2.1]hept-2-yl]-5-heptenoic acid (1.35 g, 4 mmole, prepared as described in Parts G and H) was dissolved in Et$_2$O (~30 ml) and a moderate excess of a solution of diazomethane in Et$_2$O was added. After 5 minutes, the excess diazomethane was destroyed by the addition of 2-3 drops of glacial acetic acid. After evaporation of the solvent the residue was flash-chromatographed on a column of silica gel (LP-1, 40 g) eluting the column with ether-hexane (15:85), with tlc monitoring of the fractions, to isolate slightly impure title ester (430 mg, 31%) and pure title ester (958 mg, 68%)[1] as oils with consistent IR, H$^1$-NMR and C$^{13}$-NMR spectra and $[\alpha]_D^{25} + 5.47°$ (C, 2.01; CHCl$_3$). The total yield was 99%.

Anal Calcd for $C_{21}H_{36}O_4$: C, 71.55; H, 10.29. Found: C, 71.29; H, 10.37.

270 MHz H$^1$-NMR spectrum (CDCl$_3$): δ 0.9 (t, 3H, J=8.5, CH$_3$), 1.3 (s, 8 to 9H, CH$_2$), 2.03 (m, 5H, J=~9.0, CH$_2$CH=), 2.31 (t, 2H, J=8.5, CH$_2$ COO), 3.33 (m, 4H, J=9.0, CH$_2$O), 4.66 (s, 3H, COOCH$_3$), 4.15 (d, H, J=~5.0, H$_9$), 4.38 (d, 1H, J=~5.0, H$_{12}$), 5.4 (m, 2H, J=~5.0, 14, H$_5$ and H$_6$).

1. The H$^1$-NMR spectrum showed the presence of 3.5 to 4% of the trans-double bond isomer.

J.
[1R-[1α,2β(2(R,S),5Z),3β,4α]]-7-[3-[(Hexyloxy)methyl]-7-oxabicyclo[2.2.1]hept-2-yl]-2-methyl-5-heptenoic acid, methyl ester A solution of diisopropylamine (4.0 mmole, 404 mg) in dry THF (75 ml) was cooled and stirred in a bath at −78° (dry ice-acetone) under nitrogen and 1.7M butyl-lithium in hexane (3.0 mmole, 1.8 ml) was added. After 5 minutes, a solution of the Example I ester (3.0 mmole, 1.05 g) in dry THF (12 ml) was added dropwise in the course of 5 minutes. After another 15 minutes, purified methyl iodide (neat, 12 mmole, 1.8 g) and a solution of dry hexamethyl phosphoric triamide (0.5 ml) in dry THF (1.0 ml) were added. After 1.5 hours, the solution was allowed to warm to room temperature in the course of about 30 minutes. The mixture was then poured into saturated brine (150 ml) containing concentrated hydrochloric acid (2.0 ml) and was extracted with ether (3×80 ml). The extracts were combined, washed with water, dried (MgSO$_4$ anhydrous) and evaporated to afford the crude product as an oil (1.0 g). On the basis of tlc, this was a mixture of essentially two compounds: title ester (major), and Example 60 ester (minor). In addition, minor, more polar impurities were present. This was subjected to a flash chromatography on a silica gel (LPS-1) column to isolate title ester (950 mg, 87%).

K.
[1R-[1α,2β(5Z),3β,4α]]-7-[3-[(Hexyloxy)methyl]-7-oxabicyclo[2.2.1]hept-2-yl]-2,2-dimethyl-5-heptenoic acid, methyl ester A solution of dry isopropylamine (2.0 mmole, 202 mg) in dry THF (12 ml) was cooled and stirred in a bath at −78° (dry ice-acetone) under an atmosphere of nitrogen and 1.7M n-BuLi in hexane (1.8 mmole, 1.06 ml) was added. After 5.0 minutes, a solution of [1R-[1α,2β(2(R,S),5Z),3β,4α]]-7-[3-[(hexyloxy)methyl]-7-oxabicyclo[2.2.1]hept-2-yl]-2-methyl-5-heptenoic acid, methyl ester prepared as described in Part J (1.77 mmole, 650 mg) in dry THF (6.0 ml) was added in the course of 5 minutes. After 10 minutes, purified methyl iodide (6.0 mmol, 850 mg) was added. After 1.5 hours, the solution was warmed to room temperature in the course of about 30 minutes. It was then added into 2% hydrochloric acid (75 ml) and was extracted with ether (3×40 ml). The extracts were combined, washed with water (2×20 ml), dried (MgSO$_4$ anhydrous) and evaporated to afford impure title methyl ester as an oil (640 mg, 95%). This was subjected to a flash chromatography on a silica gel (LPS-1) column to yield title ester (630 mg). The title ester was homogeneous (tlc, Et$_2$O-hexane, 1:1) and its H$^1$ and C$^{13}$-NMR spectra were consistent with the structure.

L.
[1R-[1α,2β(5Z),3β,4α]]-7-[3-[(Hexyloxy)methyl]-7-oxabicyclo[2.2.1]hept-2-yl]-2,2-dimethyl-5-heptenoic acid A solution of Part K ester (233 mg, 0.612 mmole) in dioxane (5.0 ml) was refluxed under nitrogen with LiOH.H$_2$O (150 mg) and water (5.0 ml) for 3.0 hours. The mixture was then acidified with concentrated HCl (to pH 2.5) diluted with brine (20 ml) and was extracted with ether (3×20 ml). The extracts were combined, washed with water (2×100 ml), dried (MgSO$_4$ anhydrous) and evaporated to afford the crude product as an oil (210 mg). This was subjected to a column chromatography on silica gel (Baker, 60–200 mesh, 10 g), eluting the column with hexane and Et$_2$O-hexane mixtures (15:85, 1:3) to isolate homogeneous (tlc) title acid as an oil (200 mg, 89%), $[\alpha]_D^{23}=(+)$ 1.16° (c, 2.2; CHCl$_3$), with consistent IR, mass, H$^1$- and C$^{13}$-NMR spectral data.

Anal Calcd for $C_{22}H_{38}O_4$ (MW 366.54); C, 72.08; H, 10.46. Found: C, 72.16; H, 10.37.

H$^1$-NMR Spectrum (FX-270, CDCl$_3$): δ 0.90 (t, 3H, J=~8.0, H$_{21}$), 1.23 (s, 6H, −, H$_{22}$+H$_{23}$), 2.03 (m, 4H, J=~8.0, H$_4$+H$_7$), 3.35 (m, 4H, J=~8.0, H$_{14}$+H$_{16}$), 4.20 (d, 1H, J=~4.0, H$_9$), 4.43 (d, 1H, J=~4.0, H$_{12}$), 5.35 (m, 1H, −, H$_5$+H$_6$).

M.
[1R-[1α,2β(5Z),3β,4α]]-7-[3-[(Hexyloxy)methyl]-7-oxabicyclo[2.2.1]hept-2-yl]-N-hydroxy-N,2,2-trimethyl-5-heptenamide A solution of Part L acid (300 mg; 0.82 mmol) in dry benzene (5.0 ml) was treated with oxalyl chloride (0.5 ml; 5.51 mmole) and a solution of dry dimethyl formamide (0.05 ml) in benzene (0.2 ml) and stirred at room temperature under nitrogen for 2 hours. The excess oxalyl chloride and solvent were blown off by a stream of nitrogen while heating the reaction flask in a warm water bath and the oil obtained in vacuo (oil pump) for 1 hour. The residual acid chloride was dissolved in dry tetrahydrofuran (1.5 ml) and was added into a cold solution (about 0°, ice-water) of 98% methylhydroxylamine hydrochloride (139.8 mg; 1.64 mmole) and triethylamine (0.34 ml; 2.46 mmole) in tetrahydrofuran (2 ml) and water (2.0 ml). The mixture was stirred at ~0° under nitrogen for 30 minutes, diluted with water (10 ml) and extracted twice with dichloromethane (50 ml). The organic extract was washed with 1N HCl (10 ml), 5% NaHCO$_3$ (5 ml) and water (10 ml), dried (anhydrous MgSO$_4$), filtered and evaporated to dryness giving an oil (290.5 mg) containing the desired product and traces of other components (TLC) including Part L acid. This was treated with an excess of CH$_2$N$_2$ in Et$_2$O at room temperature for 45 minutes. The excess diazomethane was blown off with a stream of nitrogen and the solution evaporated to dryness. The residual oil was chromatographed on a silica gel column (Baker 60–200 mesh; 40 ml); eluting the column with EtOAc:Hexane (1:3; 400 ml). The resulting homogeneous oily product was dissolved in ether (50 ml) and washed with 1N HCl (5 ml), followed by water (10 ml) and brine (10 ml), dried (anhydrous MgSO$_4$) filtered and evaporated to dryness to give the title compound (260 mg) as a homogeneous (TLC) oil[1] with consistent analytical data, IR (1600, 1638 Cm$^{-1}$m, strong, C=O, 3215 Cm$^{-1}$, strong, OH) mass, H$^1$- and C$^{13}$-spectral data.

Anal Calcd for C$_{23}$H$_{41}$NO$_4$: C, 69.83; N, 10.45; N, 3.54. Found: C, 69.97; N, 10.51; N, 3.46.

1. This specimen contained <2% of the trans double bond isomer.

EXAMPLE 2

(1α,2β,3β,4α)-7-[3-[(Hexyloxy)methyl]-7-oxabicyclo[2.2.1]hept-2-yl]-N-hydroxy-N,2,2-trimethyl heptanamide

A.

(1α,2β,3β,4α)-7-[3-[(Hexyloxy)methyl]-7-oxabicyclo[2.2.1]hept-2-yl]-2,2-dimethyl-5-heptanoic acid Example 1 Part L acid compound (198 mg, 0.54 mmol) is dissolved in 10 ml of methanol and is hydrogenated in the presence of 5% Pd/C (25 mg) until no double bond is visible in the $^1$H NMR spectrum.

B.

(1α,2β,3β,4α)-7-[3-[(Hexyloxy)methyl]-7-oxabicyclo[2.2.1]hept-2-yl]-N-hydroxy-N,2,2-trimethylheptanamide Following the procedure of Example 1 from Part M except substituting the above Part A acid for Example 1 Part M acid, the title compound is obtained.

EXAMPLE 3

[1R-[1α,2β(5Z),3β,4α]]-7-[3-[(Hexylthio)methyl]-7-oxabicyclo[2.2.1]hept-2-yl]-N-hydroxy-N,2,2-trimethyl-5-heptenamide

A.

[1R-[1α,2β(5Z),3β,4α]]-7-[3-(Hydroxymethyl)-7-oxabicyclo[2.2.1]hept-2-yl]-5-heptenoic acid, methyl ester The above title A compound was prepared as described in Example 1, Part F.

B.

[1R-[1α,2β(5Z),3β,4α]]-7-[3-[(Hexylthio)methyl]-7-oxabicyclo[2.2.1]hept-2-yl]-5-heptenoic acid, methyl ester A solution of 274 mg (1.02 mmol) of Part A alcohol in 2 ml of dry pyridine is cooled to 0° C. To this stirred solution is added 295 mg (1.53 mmol) of tosyl chloride. After 4 hours, the reaction mixture is diluted with 15 ml each of ether and saturated NaHCO$_3$ solution. The aqueous layer is extracted with 25 ml of ether. The combined ether layers are washed twice with 30 ml of 1N HCl, dried over MgSO$_4$, filtered, and concentrated in vacuo. The crude product is chromatographed on 32 g of silica gel using 4:1 hexane-ether as eluant. This gives pure tosylate along with a mixture of tosylate and its 5,6-double trans bond isomer.

To a solution of 105 mg (0.93 mmol) of potassium t-butoxide in 10 ml of THF is added 0.45 ml (3.1 mmol) of 1-hexanethiol. To this stirred slurry is added a solution of 270 mg (0.64 mmol) of the above tosylate in 5 ml THF. The reaction mixture is heated to reflux for 5 hours. The cooled reaction mixture is partitioned between 30 ml each of saturated NaHCO$_3$ solution and ether. The aqueous layer is extracted with 2×30 ml of ether. The combined organic extracts are dried over MgSO$_4$, filtered and concentrated in vacuo. The crude product is chromatographed on 30 g of silica gel using 4:1 hexane-ether as eluant to afford title B thioether.

C.

[1R-[1α,2β(5Z),3β,4α]]-7-[3-[(Hexylthio)methyl]-7-oxabicyclo[2.2.1]hept-2-yl]-5-heptenoic acid A solution of 222 mg (0.60 mmol) of Part B thioether in 15 ml of THF and 1.9 ml H$_2$O is purged with a stream of argon for 10 minutes. To this stirred solution is added 2.4 ml of argon-purged 1N LiOH solution. This mixture is stirred vigorously for 7 hours at room temperature. The reaction mixture is partitioned between 25 ml each of brine and EtOAc. The aqueous layer is acidified to pH=2.5 by the addition of 1N HCl and then shaken with the original EtOAc layer. The aqueous layer is extracted with 2×25 ml EtOAc. The combined EtOAc layers are dried over MgSO$_4$, filtered and concentrated in vacuo. Purification is effected by flash chromatography on 30 g of silica gel using 2:1 hexane-ether as eluant to afford title acid.

D.

[1R-[1α,2β(5Z),3β,4α]]-7-[3-[(Hexylthio)methyl]-7-oxabicyclo[2.2.1]hept-2-yl]-N-hydroxy-N,2,2,-trimethyl-5-heptenamide Following the procedure of Example 1 except substituting the above Part C acid for the Example 1 Part I acid, the title compound is obtained.

EXAMPLE 4

[1α,2β(5Z),3β,4α]-7-[3-(Methyloxy)methyl]-7-oxabicyclo[2.2.1]hept-2-yl]-N-hydroxy-N,2,2-trimethyl-5-heptenamide Following the procedure of Example 1 except substituting methyl methanesulfonate for n-hexyl methanesulfonate and the above Part C acid for Part I acid, the title compound is obtained.

EXAMPLE 5

(1α,2β,3β,4α)-7-[3-(Butyloxy)methyl]-7-oxabicyclo[2.2.1]hept-2-yl]-N-hydroxy-N-methyl heptanamide Following the procedure of Examples 1 and 2 except substituting n-butyl methanesulfonate for n-hexyl methanesulfonate in Part G and not doing parts J and K, the title compound is obtained.

EXAMPLE 6

[1α,2β(5Z),3β,4α]-7-[3-[(Octyloxy)methyl]-7-oxabicyclo[2.2.1]hept-2-yl]-N-hydroxy-N-methyl-5-heptenamide Following the procedure of Example 1 Part G (without doing Parts J and K) except substituting n-octyl methanesulfonate for n-hexyl methanesulfonate, the title compound is obtained.

EXAMPLE 7

[1α,2β(5Z),3β,4α]-7-[3-[(Phenyloxy)methyl]-7-oxabicyclo[2.2.1]hept-2-yl]-N-hydroxy-N-methyl-5-heptenamide (a) Phenol (1 mmol) is added to a solution of triphenylphosphine (1 mmol), diethylazodicarboxylate (1 mmol) and title F alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1β,2α(Z),3α,4β]-7-[3-[(phenyloxy)methyl]-7-oxabicyclo[2.2.1]hept-2-yl]-5-heptenoic acid, methyl ester.

(b) Following the procedure as set out in Example 1 Parts K, L and M, the ester from part (a) is converted to the title compound.

EXAMPLE 8

[1α,2β(5Z),3β,4α]-7-[3-[(Ethyloxy)methyl]-7-oxabicyclo[2.2.1]hept-2-yl]-N-hydroxy-N,2,2-trimethyl-5-heptenamide Following the procedure of Example 1 except substituting ethyl methanesulfonate for n-hexylmethane sulfonate in Part G, the title compound is obtained.

EXAMPLE 9

(1α,2β,3β,4α)-7-[3-[(Phenyloxy)methyl]-7-oxabicyclo[2.2.1]hept-2-yl]-N-hydroxy-N,2,2-trimethyl-5-heptanamide Following the procedure of Examples 7 and 2 except substituting the Example 7 Part A compound for the Example 1 Part L acid compound in Example 2, the title compound is obtained.

EXAMPLE 10

[1α,2β(5Z),3β,4α]-7-[3-[(Benzyloxy)methyl]-7-oxabicyclo[2.2.1]hept-2-yl]-N-hydroxy-N,2,2-trimethyl-5-heptenamide Following the procedure of Example 1 except substituting benzyl methane sulfonate for n-hexylmethane sulfonate in Part G, the title compound is obtained.

EXAMPLE 11

(1α,2β,3β,4α)-7-[3-[(Benzyloxy)methyl]-7-oxabicyclo[2.2.1]hept-2-yl]-N-hydroxy-N,2,2-trimethylheptanamide Following the procedure of Example 2 Part A except substituting the Example 1 Part G compound for the Example 1 Part L acid and then following the procedure of Example 1 Part G except substituting benzyl tosylate for n-hexyl mesylate, the title compound is obtained.

EXAMPLE 12

[1α,2β(5Z),3β,4α]-7-[3-[(Cyclohexyloxy)methyl]-7-oxabicyclo[2.2.1]hept-2-yl]-N-hydroxy-N,2,2-trimethyl-5-heptenamide Following the procedure of Example 1 except substituting cyclohexyl methanesulfonate for n-hexyl methanesulfonate in Part G, the title compound is obtained.

EXAMPLE 13

[1α,2β(5Z),3β,4α]-7-[3-[(Cyclopentyloxy)methyl]-7-oxabicyclo[2.2.1]hept-2-yl]-N-hydroxy-N,2,2-trimethyl-5-heptenamide Following the procedure of Example 1 except substituting cyclopentyl methanesulfonate for n-hexyl methanesulfonate in Part G, the title compound is obtained.

EXAMPLE 14

(1α,2β,3β,4α)-7-[3-[(Cyclohexyloxy)methyl]-7-oxabicyclo[2.2.1]hept-2-yl]-N-hydroxy-N,2,2-trimethylheptanamide Following the procedure of Example 2 except substituting the acid prepared in Example 12 acid for the Example 1 Part I acid, the title compound is obtained.

EXAMPLE 15

[1α,2β(5Z),3β,4α]-7-[3-[2-(Hexyloxy)ethyl]-7-oxabicyclo[2.2.1]hept-2-yl]-N-hydroxy-N,2,2-trimethyl-5-heptenamide

A.

[1α,2β(5Z),3β,4α]-7-[[3-(2-Oxo)ethyl]-7-oxabicyclo[2.2.1]hept-2-yl]-5-heptenoic acid, methyl ester Into a dry 100 ml round bottom 3-necked flask containing a stir bar is added dried methoxymethyltriphenylphosphonium chloride (($C_6H_5)_3P^+$-$CH_2OCH_3Cl^-$) (12.9 g, 37.7 mmol) and 235 ml distilled toluene (stored over molecular sieves). The resulting suspension is stirred in an ice-bath, under argon, until cold and then a 1.55M solution of 18.3 ml (28.3 mmol) of potassium t-amylate in toluene was added dropwise. A bright red solution formed which is stirred at 0° C. for an additional 35 minutes. Thereafter, a solution of 4.8 g (18.8 mmol) [1β,2α(5Z),3α,4β]-7-(3-formyl)-7-oxabicyclo[2.2.1]hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) of acetic acid in 5 ml ether. The reaction mixture is immediately poured into 200 ml saturated $NH_4Cl$, and extracted with ether (4×200 ml). The combined ether phases are washed with NaCl saturated solution, and dried ($MgSO_4$) and concentrated to yield a yellow oil in a white crystalline solid (phosphine oxide). This is washed with EtOAc and the material in the washings is purified by chromatography on an LPS-1 silica gel column. The fractions obtained are (A) [1β,2α(5Z)-,3α,4β]-7-[[3-(2-oxo)ethyl]-7-oxabicyclo[2.2.1]hept-2-yl]-5-heptenoic acid, methyl ester, (B) [1β,2α(5Z)-,3α,4β]-7-[3-(2-methoxy)ethendiyl]-7-oxabicyclo[2.2.1]hept-2-yl]-5-heptenoic acid, methyl ester, and (C) [1β,2α(5Z),3α,4β]-7-[[3-(2,2-dimethoxy)ethyl]-7-oxabicyclo[2.2.1]hept-2-yl]-5-heptenoic acid, methyl ester.

Compounds (B) and (C) are each treated with trifluoroacetic acid to convert each to compound (A).

B.

[1α,2β(5Z),3β,4α]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.

[1α,2β(5Z),3β,4α]-7-[3-(2-(Hexyloxy)ethyl]-7-oxabicyclo[2.2.1]hept-2-yl]-2,2-dimethyl-5-heptenoic acid Following the procedure of Example 1 Parts G to L except substituting the above part B alcohol for the alcohol used in Example 1 Part G, the title compound is obtained.

D.

[1α,2β(5Z),3β,4α]-7-[3-[2-(Hexyloxy)ethyl]-7-oxabicyclo[2.2.1]hept-2-yl]-N-hydroxy-N,2,2-trimethyl-5-heptenamide Following the procedure of Example 1 Part M except substituting the above Part C acid for the Example 1 Part L acid, the title compound is obtained.

EXAMPLE 16

(1α,2β,3β,4α)-7-[3-[2-(Hexyloxy)ethyl]-7-oxabicyclo[2.2.1]hept-2-yl]-N-hydroxy-N,2,2-trimethylheptanamide Following the procedure of Examples 15 and 2 except substituting (1β,2α,3α,4β)-7-[(3-formyl)-7-oxabicyclo[2.2.1]hept-2-yl]-5-heptanoic acid, methyl ester for [1β,2α(Z),3α,4β]-7-[(3-formyl)-7-oxabicyclo[2.2.1]hept-2-yl]-5-heptenoic acid, methyl ester, the title compound is obtained.

EXAMPLE 17

(1α,2β,3β,4α)-7-[3-[2-(Phenyloxy)ethyl]-7-oxabicyclo[2.2.1]hept-2-yl]-N-hydroxy-N,2,2-trimethylheptanamide Following the procedure of Examples 7, 16 and 2 except substituting (1α,2β,3β,4α)-7-[3-[2-(hydroxy)ethyl]-7-oxabicyclo[2.2.1]hept-2-yl]heptanoic acid, methyl ester for [1α,2β(5Z),3β,4α]-7-[3-(hydroxymethyl)-7-oxabicyclo[2.2.1]hept-2-yl]-5-heptenoic acid, methyl ester, the title compound is obtained.

EXAMPLE 18

[1α,2β(5Z),3β,4α]-7-[3-[2-(Benzyloxy)ethyl]-7-oxabicyclo[2.2.1]hept-2-yl]-N-hydroxy-N,2,2-trimethyl-5-heptenamide Following the procedure of Example 15 except substituting benzyl methanesulfonate for n-hexyl methanesulfonate, the title compound is obtained.

EXAMPLE 19

[1α,2β(5Z),3β,4α]-7-[3-[2-(Cyclopentyloxy)ethyl]-7-oxabicyclo[2.2.1]hept-2-yl]-N-hydroxy-N,2,2-trimethyl-5-heptenamide Following the procedure of Example 15 except substituting cyclopentyl methanesulfonate for n-hexyl methansulfonate, the title compound is obtained.

EXAMPLE 20

[1α,2β(5Z),3β,4α]-7-[3-[2-(Cyclohexyloxy)ethyl]-7-oxabicyclo[2.2.1]hept-2-yl]-N-hydroxy-N,2,2-trimethyl-5-heptenamide Following the procedure of Example 15 except substituting cyclohexyl methanesulfonate for n-hexyl methanesulfonate, the title compound is obtained.

EXAMPLE 21

[1α,2β(5Z),3β,4α]-7-[3-[4-(Hexyloxy)butyl]-7-oxabicyclo[2.2.1]hept-2-yl]-N-hydroxy-N,2,2-trimethyl-5-heptenamide

A.

[1α,2β(5Z),3β,4α]-7-[[3-(3-Oxo)propyl]-7-oxabicyclo[2.2.1]hept-2-yl]-5-heptenoic acid, methyl ester Following the procedure of Example 15, part A except substituting [1α,2β(5Z),3β,4α]-7-[[3-(2-oxo)ethyl]-7-oxabicyclo[2.2.1]hept-2-yl]-5-heptenoic acid, methyl ester for [1β,2α(5Z),3α,4β]-7-[[3-formyl]-7-oxabicyclo[2.2.1]hept-2-yl]-5-heptenoic acid, methyl ester, the title A compound is obtained.

B.

[1α,2β(5Z),3β,4α]-7-[3-(4-Oxo)butyl-7-oxabicyclo[2.2.1]hept-2-yl]-5-heptenoic acid, methyl ester Following the procedure of Example 15, part A, except substituting the aldehyde from part A above for [1α,2β(5Z),3β,4α]-7-[[3-formyl]-7-oxabicyclo[2.2.1]hept-2-yl]-5-heptenoic acid, methyl ester, the title B compound is obtained.

C.

[1α,2β(5Z),3β,4α]-7-[3-(4-Hydroxybutyl)-7-oxabicyclo[2.2.1]hept-2-yl]-5-heptenoic acid, methyl ester Following the procedure of Example 15, part B, except substituting the title B aldehyde for [1α,2β(5Z),3β,4α]-7-[[3-(2-oxoethyl)-7-oxabicyclo[2.2.1]hept-2-yl]-5-heptenoic acid, methyl ester, the title C alcohol is obtained.

D.

[1α,2β(5Z),3β,4α]-7-[3-[4-(Hexyloxy)butyl]-7-oxabicyclo[2.2.1]hept-2-yl]-5-heptenoic acid Following the procedure of Example 1, except substituting the above part C alcohol for the alcohol used in Example 1 Part G, the title compound is obtained.

E.

[1α,2β(5Z),3β,4α]-7-[3-[4-(Hexyloxy)butyl]-7-oxabicyclo[2.2.1]hept-2-yl]-N-hydroxy-N,2,2-trimethyl-5-heptenamide Following the procedure of Example 1M except substituting the above Part D acid for Example 1 Part I acid, the title compound is obtained.

EXAMPLE 22

[1α,2β(5Z),3β,4α]-7-[3-[4-(Cyclohexyloxy)butyl]-7-oxabicyclo[2.2.1]hept-2-yl]-5-heptenamide Following the procedure of Example 21 except substituting cyclohexyl methanesulfonate for n-hexyl methanesulfonate, the title compound is obtained.

EXAMPLE 23

[1α,2β(5Z),3β,4α]-7-[3-[4-(Phenyloxy)butyl]-7-oxabicyclo[2.2.1]hept-2-yl]-N-hydroxy-N,2,2-trimethyl-5-heptenamide Following the procedure of Examples 9 and 21 except substituting [1α,2β(5Z),3β,4α]-7-[3-(4-hydroxybutyl)-7-oxabicyclo[2.2.1]hept-2-yl]-5-heptenoic acid, methyl ester for [1α,2β(5Z),3β,4α]-7-[3-(hydroxymethyl)-7-oxabicyclo[2.2.1]hept-2-yl]-5-heptenoic acid, methyl ester, the title compound is obtained.

EXAMPLE 24

[1α,2β(5Z),3β,4α]-7-[3-[4-(Benzyloxy)butyl]-7-oxabicyclo[2.2.1]hept-2-yl]-N-hydroxy-N,2,2-trimethyl-5-heptenamide Following the procedure of Example 21 except substituting benzyl methanesulfonate for n-hexyl methanesulfonate, the title compound is obtained.

EXAMPLE 25

[1α,2β(5Z),3β,4α]-7-[3-[(Methylthio)methyl]-7-oxabicyclo[2.2.1]hept-2-yl]-N-hydroxy-N,2,2-trimethyl-5-heptenamide Following the procedure of Example 3 except substituting methyl mercaptan for 1-hexanethiol, the title compound is obtained.

EXAMPLE 26

[1α,2β(5Z),3β,4α]-7-[3-[(Propylthio)methyl]-7-oxabicyclo[2.2.1]hept-2-yl]-N-hydroxy-N,2,2-trimethyl-5-heptenamide Following the procedure of Example 3 except substituting propylmercaptan for 1-hexanethiol, the title compound is obtained.

EXAMPLE 27

(1α,2β,3β,4α)-7-[3-(Butylthio)methyl]-7-oxabicyclo[2.2.1]hept-2-yl]-N-hydroxy-N,2,2-trimethylheptanamide Following the procedure of Examples 3 and 2 except substituting butylmercaptan for 1-hexanethiol, the title compound is obtained.

EXAMPLE 28

[1α,2β(5Z),3β,4α]-7-[3-[(Octylthio)methyl]-7-oxabicyclo[2.2.1]hept-2-yl]-N-hydroxy-N,2,2-trimethyl-5-heptenamide Following the procedure of Example 3 except substituting 1-octanethiol for 1-hexanethiol, the title compound is obtained.

EXAMPLE 29

[1α,2β(5Z),3β,4α]-7-[3-[(Phenylthio)methyl]-7-oxabicyclo[2.2.1]hept-2-yl]-N-hydroxy-N,2,2-trimethyl-5-heptenamide Following the procedure of Example 3 except substituting phenylmercaptan for 1-hexanethiol, the title compound is obtained.

EXAMPLE 30

(1α,2β,3β,4α)-7-[3-[(Phenylthio)methyl]-7-oxabicyclo[2.2.1]hept-2-yl]-N-hydroxy-N,2,2-trimethylheptanamide Following the procedure of Examples 3 and 2 except substituting phenylmercaptan for 1-hexanethiol, the title compound is obtained.

EXAMPLE 31

[1α,2β(5Z),3β,4α]-7-[3-[(Ethylthio)methyl]-7-oxabicyclo[2.2.1]hept-2-yl]-N-hydroxy-N,2,2-trimethyl-5-heptenamide Following the procedure of Example 3 except substituting ethylmercaptan for 1-hexanethiol, the title compound is obtained.

EXAMPLE 32

[1α,2β(5Z),3β,4α]-7-[3-[(Benzylthio)methyl]-7-oxabicyclo[2.2.1]hept-2-yl]-N-hydroxy-N,2,2-trimethyl-5-heptenamide Following the procedure of Example 3 except substituting benzylmercaptan for 1-hexanethiol, the title product is obtained.

EXAMPLE 33

[1α,2β(5Z),3β,4α]-7-[3-[(Cyclohexylthio)methyl]-7-oxabicyclo[2.2.1]hept-2-yl]-N-hydroxy-N,2,2-trimethyl-5-heptenamide Following the procedure of Example 3 except substituting cyclohexylmercaptan for 1-hexanethiol, the title compound is obtained.

EXAMPLE 34

(1α,2β,3β,4α)-7-[3-[(Cyclohexylthio)methyl]-7-oxabicyclo[2.2.1]hept-2-yl]-N-hydroxy-N,2,2-trimethylheptanamide Following the procedure of Examples 3 and 2 except substituting cyclohexylmercaptan for 1-hexanethiol, the title product is obtained.

EXAMPLE 35

[1α,2β(5Z),3β,4α]-7-[3-[2-(Hexylthio)ethyl]-7-oxabicyclo[2.2.1]hept-2-yl]-N-hydroxy-N,2,2-trimethyl-5-heptenamide Following the procedure of Examples 15 and 3 except substituting the Example 15 part B alcohol for the alcohol used in Example 3, the title compound is obtained.

EXAMPLE 36

(1α,2β,3β,4α)-7-[3-[2-(Hexylthio)ethyl]-7-oxabicyclo[2.2.1]hept-2-yl]-N-hydroxy-N,2,2-trimethylheptanamide Following the procedure of Examples 15, 16, 2, and 3 except substituting the Example 15 Part B alcohol for the alcohol used in Example 3 Part A, the title compound is obtained.

EXAMPLE 37

[1α,2β(5Z),3β,4α]-7-[3-[2-(Phenylthio)ethyl]-7-oxabicyclo[2.2.1]hept-2-yl]-N-hydroxy-N,2,2-trimethyl-5-heptenamide Following the procedure of Examples 15, 16 and 3 except substituting the Example 15 Part B alcohol for the alcohol used in Example 3, Part A and substituting phenylmercaptan for 1-hexanethiol (of Example 3), the title compound is obtained.

EXAMPLE 38

(1α,2β,3β,4α)-7-[3-[2-(Phenylthio)ethyl]-7-oxabicyclo[2.2.1]hept-2-yl]-N-hydroxy-N,2,2-trimethylheptanamide Following the procedure of Examples 15, 16, 2 and 3 except substituting the Example 15 Part B alcohol for the alcohol used in Example 3, Part A and substituting phenylmercaptan for 1-hexanethiol (of Example 3), the title compound is obtained.

EXAMPLE 39

[1α,2β(5Z),3β,4α]-7-[3-[2-(Cyclopentylthio)ethyl]-7-oxabicyclo[2.2.1]hept-2-yl]-N-hydroxy-N,2,2-trimethyl-5-heptenamide Following the procedure of Examples 15 and 3 except substituting the Example 15B alcohol for the alcohol used in Example 3, Part A and substituting cyclopentylmercaptan for 1-hexanethiol (of Example 3), the title compound is obtained.

EXAMPLE 40

[1α,2β(5Z),3β,4α]-7-[3-[2-(Cyclohexylthio)ethyl]-7-oxabicyclo[2.2.1]hept-2-yl]-N-hydroxy-N,2,2-trimethyl-5-heptenamide Following the procedure of Example 16 except substituting the Example 15B alcohol for the alcohol used in Example 3, Part A and substituting cyclohexylmercaptan for 1-hexanethiol (of Example 3), the title product is obtained.

EXAMPLE 41

[1α,2β(5Z),3β,4α]-7-[3-[4-(Hexylthio)butyl]-7-oxabicyclo[2.2.1]hept-2-yl]-N-hydroxy-N,2,2-trimethyl-5-heptenamide Following the procedure of Examples 21 and 3 except substituting the Example 21 part C alcohol for the alcohol used in Example 3, the title compound is obtained.

EXAMPLE 42

[1α,2β(5Z),3β,4α]-7-[3-[4-(Cyclohexylthio)butyl]-7-oxabicyclo[2.2.1]hept-2-yl]-N-hydroxy-N,2,2-trimethyl-5-heptenamide Following the procedure of Example 41 except substituting cyclohexylmercaptan for 1-hexanethiol, the title compound is obtained.

EXAMPLE 43

[1α,2β(5Z),3β,4α]-7-[3-[4-(Phenylthio)butyl]-7-oxabicyclo[2.2.1]hept-2-yl]-N-hydroxy-N,2,2-trimethyl-5-heptenamide Following the procedure of Example 41 except substituting phenylmercaptan for 1-hexanethiol, the title compound is obtained.

EXAMPLE 44

[1α,2β(5Z),3β,4α]-7-[3-[4-(Benzylthio)butyl]-7-oxabicyclo[2.2.1]hept-2-yl]-N-hydroxy-N,2,2-trimethyl-5-heptenamide Following the procedure of Example 41 except substituting benzylmercaptan for 1-hexanethiol, the title compound is obtained.

EXAMPLES 45 AND 46

[1α,2β(5Z),3β,4α]-7-[3-[(Hexylsulfinyl)methyl]-7-oxabicyclo[2.2.1]hept-2-yl]-N-hydroxy-N,2,2-trimethyl-5-heptenamide (Example 45) and

[1α,2β(5Z),3β,4α]-7-[3-[(Hexylsulfonyl)methyl]-7-oxabicyclo[2.2.1]hept-2-yl]-N-hydroxy-N,2,2-trimethyl-5-heptenamide (Example 46)

To a solution of 634 mg (1.72 mmol) of [1α,2β(5Z),3β,4α]-7-[3-([hexylthio)methyl]-7-oxabicyclo[2.2.1]hept-2-yl]-2,2-dimethyl-5-heptenoic acid, methyl ester (prepared as described in Example 3) in 6.78 ml of methanol at 0° C. is added dropwise over 4 minutes 4.8 ml of 0.5M aqueous sodium periodate solution. Tetrahydrofuran (2 ml) is then added and the resulting reaction mixture is stirred at room temperature for 15 hours. A precipitate is removed by filtration and washed with ether (3×50 ml). The filtrate is washed with 60 ml of saturated aqueous NaHCO$_3$ solution and dried over anhydrous magnesium sulfate. Concentration in vacuo affords an oily crude product. This is chromatographed on silica gel 60 using 0.5–1.0% CH$_3$OH in CH$_2$Cl$_2$ as eluant. This gives [1α,2β(5Z),3β,4α]-7-[3-[(hexylsulfinyl)methyl]-7-oxabicyclo[2.2.1]hept-2-yl]-2,2-dimethyl-5-heptenoic acid, methyl ester (Example 45) [1α,2β(5Z),3β,4α]-7-[3-[(hexylsulfonyl)methyl]-7-oxabicyclo[2.2.1]hept-2-yl]-2,2-dimethyl-5-heptenoic acid, methyl ester (Example 46).

Following the procedure as described in Example 1 Part M except substituting the above sulfide and sulfone for the Example 1 Part L acid, the title compounds are obtained.

EXAMPLE 47

[1α,2β(5Z),3β,4α]-7-[3-[(Methylsulfinyl)methyl]-7-oxabicyclo[2.2.1]hept-2-yl]-N-hydroxy-N,2,2-trimethyl-5-heptenamide Following the procedure of Examples 3 and 45 except substituting methyl mercaptan for 1-hexanethiol, the title compound is obtained.

EXAMPLE 48

[1α,2β(5Z),3β,4α]-7-[3-[(Octylsulfinyl)methyl]-7-oxabicyclo[2.2.1]hept-2-yl]-N-hydroxy-N,2,2-trimethyl-5-heptenamide Following the procedure of Examples 3 and 46 except substituting 1-octanethiol for 1-hexanethiol, the title compound is obtained.

EXAMPLE 49

[1α,2β(5Z),3β,4α]-7-[3-[(Ethylsulfinyl)methyl]-7-oxabicyclo[2.2.1]hept-2-yl]-N-hydroxy-N,2,2-trimethyl-5-heptenamide Following the procedure of Examples 3 and 45 except substituting ethylmercaptan for 1-hexanethiol, the title compound is obtained.

EXAMPLE 50

(1α,2β,3β,4α)-7-[3-[(Heptylsulfinyl)methyl]-7-oxabicyclo[2.2.1]hept-2-yl]-N-hydroxy-N,2,2-trimethylheptanamide Following the procedure of Examples 3, 2, and 45 except substituting 1-heptanethiol for 1-hexanethiol, the title compound is obtained.

EXAMPLE 51

[1α,2β(5Z),3β,4α]-7-[3-[(Benzylsulfinyl)methyl]-7-oxabicyclo[2.2.1]hept-2-yl]-N-hydroxy-N,2,2-trimethyl-5-heptenamide Following the procedure of Examples 3 and 45 except substituting benzylmercaptan for 1-hexanethiol, the title compound is obtained.

EXAMPLE 52

[1α,2β(5Z),3β,4α]-7-[3-[(Cyclohexylmethylsulfinyl)methyl]-7-oxabicyclo[2.2.1]hept-2-yl]-N-hydroxy-N,2,2-trimethyl-5-heptenamide Following the procedure of Examples 3 and 45 except substituting cyclohexylmethyl mercaptan for 1-hexanethiol, the title compound is obtained.

EXAMPLE 53

[1α,2β(5Z),3β,4α]-7-[3-[(Cyclopentylethylsulfinyl)methyl]-7-oxabicyclo[2.2.1]hept-2-yl]-N-hydroxy-N,2,2-trimethyl-5-heptenamide Following the procedure of Examples 3 and 45 except substituting cyclopentylethyl mercaptan for 1-hexanethiol, the title compound is obtained.

EXAMPLE 54

[1α,2β(5Z),3β,4α]-7-[3-[(Octylsulfonyl)methyl]-7-oxabicyclo[2.2.1]hept-2-yl]-N-hydroxy-N,2,2-trimethyl-5-heptenamide Following the procedure of Examples 3 and 46 except substituting octylmercaptan for 1-hexanethiol, the title compound is obtained.

EXAMPLE 55

[1α,2β(5Z),3β,4α]-7-[3-[(Propylsulfonyl)methyl]-7-oxabicyclo[2.2.1]hept-2-yl]-N-hydroxy-N,2,2-trimethyl-5-heptenamide Following the procedure of Examples 3 and 46 except substituting propylmercaptan for 1-hexanethiol, the title compound is obtained.

EXAMPLE 56

[1α,2β(5Z),3β,4α]-7-[3-[(Phenylsulfonyl)methyl]-7-oxabicyclo[2.2.1]hept-2-yl]-N-hydroxy-N,2,2-trimethyl-5-heptenamide Following the procedure of Examples 3 and 46 except substituting phenylmercaptan for 1-hexanethiol, the title compound is obtained.

EXAMPLE 57

[1α,2β(5Z),3β,4α]-7-[3-[(Benzylsulfonyl)methyl]-7-oxabicyclo[2.2.1]hept-2-yl]-N-hydroxy-N,2,2-trimethyl-5-heptenamide Following the procedure of Examples 3 and 46 except substituting benzylmercaptan for 1-hexanethiol, the title compound is obtained.

EXAMPLE 58

[1α,2β(5Z),3β,4α]-7-[3-[(Cyclohexylsulfonyl)methyl]-7-oxabicyclo[2.2.1]hept-2-yl]-N-hydroxy-N,2,2-trimethyl-5-heptenamide Following the procedure of Examples 3 and 46 except substituting cyclohexylmercaptan for 1-hexanethiol, the title compound is obtained.

EXAMPLE 59

(1α,2β,3β,4α)-7-[3-[(Cyclopropylmethylsulfinyl)methyl]-7-oxabicyclo[2.2.1]hept-2-yl]-N-hydroxy-N,2,2-trimethylheptanamide Following the procedure of Examples 3, 2, and 45 except substituting cyclopropylmercaptan for 1-hexanethiol, the title compound is obtained.

EXAMPLE 60

[1α,2β(5Z),3β,4α]-7-[3-[2-(Pentylsulfinyl)ethyl]-7-oxabicyclo[2.2.1]hept-2-yl]-N-hydroxy-N,2,2-trimethyl-5-heptenamide Following the procedure of Examples 35, 3, and 45 except substituting 1-pentanethiol for 1-hexanethiol, the title compound is obtained.

EXAMPLE 61

[1α,2β(5Z),3β,4α]-7-[3-[2-(Phenylsulfonyl)ethyl]-7-oxabicyclo[2.2.1]hept-2-yl]-N-hydroxy-N,2,2-trimethyl-5-heptenamide Following the procedure of Examples 35, 3, and 46 except substituting phenylmercaptan for 1-hexanethiol, the title compound is obtained.

EXAMPLE 62

[1α,2β(5Z),3β,4α]-7-[3-[2-(Cyclohexylsulfonyl)ethyl]-7-oxabicyclo[2.2.1]hept-2-yl]-N-hydroxy-N,2,2-trimethyl-5-heptenamide Following the procedure of Examples 35, 3, and 46 except substituting cyclohexylmercaptan for 1-hexanethiol, the title compound is obtained.

EXAMPLE 63

[1α,2β(5Z),3β,4α]-7-[3-[2-(Benzylsulfinyl)ethyl]-7-oxabicyclo[2.2.1]hept-2-yl]-N-hydroxy-N,2,2-trimethyl-5-heptenamide Following the procedure of Examples 35, 3, and 46 except substituting benzylmercaptan for 1-hexanethiol, the title compound is obtained.

EXAMPLE 64

[1α,2β(5Z),3β(E),4α]-7-[3-[[(4-Phenyl-2-butenyl)thio]-methyl]-7-oxabicyclo[2.2.1]hept-2-yl]-N-hydroxy-N,2,2-trimethyl-5-heptenamide Following the procedure of Example 3 except substituting 4-phenyl-2-butenylthiol for 1-hexanethiol, the title compound is obtained.

EXAMPLE 65

[1α,2β(5Z),3β(E),4α]-7-[3-[[(3-Cyclohexyl-2-propenyl)oxy]methyl]-7-oxabicyclo[2.2.1]hept-2-yl]-N-hydroxy-N,2,2-trimethyl-5-heptenamide Following the procedure of Example 1 except substituting (E)-3-cyclohexyl-2-propenylmesylate for 1-hexyl mesylate, the title compound is obtained.

EXAMPLE 66

[1α,2β(5Z),3β,4α]-7-[3-[[(2,3-Dimethyl-2-heptenyl)oxy]methyl]-7-oxabicyclo[2.2.1]hept-2-yl]-N-hydroxy-N,2,2-trimethyl-5-heptenamide Following the procedure of Examples 3 and 1 except substituting 2,3-dimethyl-2-heptenylmesylate for 1-hexyl mesylate, the title compound is obtained.

EXAMPLE 67

[1α,2β(5Z),3β,4α]-7-[3-[[(3-Ethyl-3-octenyl)thio]methyl]-7-oxabicyclo[2.2.1]hept-2-yl]-N-hydroxy-N,2,2-trimethyl-5-heptenamide Following the procedure of Example 3 except substituting 3-ethyl-3-octenylthiol for 1-hexanethiol, the title compound is obtained.

EXAMPLE 68

[1α,2β(5Z),3β,4α]-7-[3-[[(8-Phenyl-5-octynyl)thio]methyl]-7-oxabicyclo[2.2.1]hept-2-yl]-N-hydroxy-N,2,2-trimethyl-5-heptenamide Following the procedure of Example 3 except substituting 8-phenyl-5-octynylthiol for 1-hexanethiol, the title compound is obtained.

EXAMPLE 69

[1α,2β(5Z),3β,4α]-7-[3-[[(9-Cyclohexyl-3-nonynyl)oxy]methyl]-7-oxabicyclo[2.2.1]hept-2-yl]-N-hydroxy-N,2,2-trimethyl-5-heptenamide Following the procedure of Example 1 except substituting 9-cyclohexyl-3-nonynylmesylate for 1-hexylmesylate, the title compound is obtained.

EXAMPLE 70

[1α,2β(5Z),3β,4α]-7-[3-[[2-(3-Phenyl-2-propenyl)thio]ethyl]-7-oxabicyclo[2.2.1]hept-2-yl]-N-hydroxy-N,2,2-trimethyl-5-heptenamide Following the procedure of Examples 15 and 3 except substituting the Example 15 part B alcohol for the alcohol used in Example 3 Part B and substituting 3-phenyl-2-propenylthiol for 1-hexanethiol, the title compound is obtained.

EXAMPLE 71

[1α,2β(5Z),3β,4α]-7-[3-[[2-(6-Phenyl-3-hexynyl)oxy]ethyl]-7-oxabicyclo[2.2.1]hept-2-yl]-N-hydroxy-N,2,2-trimethyl-5-heptenamide Following the procedure of Examples 15 and 1 except substituting 6-phenyl-3-hexynylmesylate for 1-hexylmesylate, the title compound is obtained.

EXAMPLE 72

[1α,2β(5Z),3β,4α]-7-[3-[[2-(3-Cycloheptyl-2-propenyl)thio]ethyl]-7-oxabicyclo[2.2.1]hept-2-yl]-N-hydroxy-N,2,2-trimethyl-5-heptenamide Following the procedure of Examples 3, 2 and 15 except substituting 3-cycloheptyl-2-propenylthiol for 1-hexanethiol, the title compound is obtained.

EXAMPLE 73

[1α,2β(5Z),3β,4α]-7-[3-[[4-(3-Phenyl-2-propenyl)thio]butyl]-7-oxabicyclo[2.2.1]hept-2-yl]-N-hydroxy-N,2,2-trimethyl-5-heptenamide Following the procedure of Examples 41 and 3 except substituting the Example 21 Part C alcohol for the alcohol used in Example 3 and substituting 3-phenyl-2-propenylthiol for 1-hexanethiol, the title compound is obtained.

EXAMPLE 74

[1α,2β(5Z),3β,4α]-7-[3-[[4-(6-Phenyl-3-hexynyl)oxy]butyl]-7-oxabicyclo[2.2.1]hept-2-yl]-N-hydroxy-N,2,2-trimethyl-5-heptenamide Following the procedure of Examples 21 and 1 except substituting 6-phenyl-3-hexynylmesylate for 1-hexylmesylate, the title compound is obtained.

EXAMPLE 75

[1α,2β(5Z),3β,4α]-7-[3-[[4-(7-Phenyl-3-heptenyl)thio]butyl]-7-oxabicyclo[2.2.1]hept-2-yl]-N-hydroxy-N,2,2-trimethyl-5-heptenamide Following the procedure of Examples 73 and 3 except substituting 7-phenyl-3-heptenylthiol for 3-phenyl-2-propenylthiol, the title compound is obtained.

EXAMPLE 76

[1α,2β(5Z),3β,4α]-7-[3-[[4-(7-Heptynyl)thio]butyl]-7-oxabicyclo[2.2.1]hept-2-yl]-N-hydroxy-N,2,2,-trimethyl-5-heptenamide Following the procedure of Examples 3 and 23 except substituting 7-heptynylthiol for 3-phenyl-2-propenylthiol, the title compound is obtained.

EXAMPLE 77

[1R-[1α,2β(3Z),3β,4α]-5-[3-[(Hexyloxy)methyl]-7-oxabicyclo[2.2.1]hept-2-yl]-pent-3-enoic acid A. 3-Bromo-1-tetrahydropyranyloxy propane A solution of 3-bromo-1-propanol (10 mmole) in dichloromethane (20 ml) containing pyridinium p-toluene sulfonate (150 mg) is stirred with dihydropyran (15 mmole) for 20 hours at ambient temperature. The solution is then washed with water, dried (MgSO4 anhydrous), evaporated and is chromatographed on silica gel to afford the title compound.

B.
1-Tetrahydropyranyloxypropyl-3-(triphenyl)phosphonium bromide

A solution of Part A compound (5 mmol) is refluxed with triphenylphosphine (5 mmol) under nitrogen in acetonitrile (30 ml) for 20 hours. The mixture is then concentrated and is diluted with dry ether to precipitate the title compound as a colorless solid. This is dried in vacuo prior to use.

C.
[1R-[1α,2β(3Z),3β,4α]-5-[3-[(Hydroxy)methyl]-1-tetrahydropyranyloxy-7-oxabicyclo[2.2.1]hept-2-yl]-pent-3-enol To a stirred mixture of Part B phosphonium salt (5.5 mmole) and Example 1, Part E hemiacetal (5 mmol) in dry tetrahydrofuran (25 ml) in an ice bath is added a 1M solution of K-t-amylate in toluene (6 mmole). The mixture is then stirred at room temperature for 20 hours and is made acidic by the addition of a few drops of acetic acid. It is then concentrated in vacuo, diluted with water and is extracted with ethyl acetate. The extracts are combined, washed with water, dried (MgSO$_4$ anhydrous), evaporated and the residue is chromatographed on silica gel to isolate the title compound.

D.
[1R-[1α-2β(3Z),3β,4α]-5-[3-[(Hexyloxy)methyl]-1-tetrahydropyranyloxy-7-oxabicyclo[2.2.1]hept-2-yl]-pent-3-enol Part C compound (5 mmol) is reacted with n-hexylmesylate as described in Example 1, Part G to afford the title compound.

E.
[1R-[1α,2β(3Z),3β,4α]-5-[3-[(Hexyloxy)methyl]-7-oxabicyclo[2.2.1]hept-2-yl]-pent-3-enol A solution of Part D compound (5 mmole) in methanol (25 ml) containing pyridinium p-toluene sulfonate (150 mg) is refluxed for 4 hours. The solution is then concentrated in vacuo, diluted with water and is extracted with ethyl acetate. The extracts are combined, washed with a dilute sodium bicarbonate solution and water, dried (MgSO$_4$ anhydrous) and is evaporated to an oil. This is chromatographed on silica gel to afford the title compound.

F.
[1R-[1α,2β(3Z),3β,4α]-5-[3-[(Hexyloxy)methyl]-7-oxabicyclo[2.2.1]hept-2-yl]-pent-3-enoic acid A solution of Part F alcohol (5 mmol) in acetone (30 ml) is stirred in an ice bath and a modest excess of Jones reagent is added dropwise. After 1 hour, the mixture is diluted with water (150 ml) and is extracted with ethyl acetate. The extracts are combined, washed several times with small amounts of water, dried (MgSO$_4$) and is evaporated to afford the crude product as an oil. This is chromatographed on silica gel to isolate the title compound.

EXAMPLE 78
[1R-[1α,2β(2E),3β,4α]-4-[3-(Hexyloxy)methyl]-7-oxabicyclo[2.2.1]hept-2-yl]-but-2-enoic acid

A.
[1R-[1α,2β(2E),3β,4α]-4-[3-(Hydroxy)methyl]-7-oxabicyclo[2.2.1]hept-2-yl]but-2-enoic acid, methyl ester A solution of trimethyl phosphono acetate (5 mmol) in dry tetrahydrofuran (20 ml) is stirred in an ice bath for 1 hour with 50% sodium hydride/paraffin (5 mmole). A solution of Example 1, Part E hemiacetal is then added and the mixture is stirred in the ice bath for 20 hours. It is then concentrated in vacuo and diluted with water. The product is isolated by extraction with ethyl acetate and is purified by chromatography to afford the title compound.

B.
[1R-[1α,2β(2E),3β,4α]-4-[3-(Hexyloxy)methyl]-7-oxabicyclo[2.2.1]hept-2-yl]-but-2-enoic acid Part A ester (5 mmole) and n-hexylmesylate are reacted as described in Example 1, Part G and the crude product is hydrolyzed with lithium hydroxide as described in Example 1, Part L to afford the title compound after chromatography on silica gel.

EXAMPLES 78 TO 89

Following the procedure of Example 1 except replacing the 4-carboxybutyl triphenylphosphonium bromide with the compound shown in Column I, replacing n-hexylmesylate in Example 1 Part G with the compound shown in Column II of Table I set out below and replacing methylhydroxylamine in Example 1 Part M with the compound shown in Column III, the product shown in Column IV is obtained (wherein A is —CH=CH—).

TABLE 1

| Ex. No. | Column I<br>Br⁻(C₆H₅)₃P⁺—(CH₂)ₘ—COOH<br>m | Column II<br>R²Br<br>R² | Column III<br>HN—OR¹<br>\|<br>R<br>R | R¹ | Column IV<br>$\begin{array}{c}\text{bicyclic epoxide with}\\ CH_2-CH=CH-(CH_2)_m-C(O)-N(R)-OR^1\\ CH_2-O-R^2\end{array}$ |
|---|---|---|---|---|---|
| 78. | 3 | C₂H₅ | H | C₃H₇ | m as in Column I; R² as in Column II; R, R¹ as in Column III |
| 79. | 4 | C₆H₅ | H | C₄H₉ | |
| 80. | 4 | —CH₂C₆H₅ | C₃H₇ | C₆H₅ | |
| 81. | 1 | (cyclohexyl) | H | C₆H₅CH₂ | |
| 82. | 4 | —CH₂-(cyclohexyl) | H | (cyclohexyl) | |
| 83. | 5 | —CH₂—CH=CH—CH₃ | C₂H₅ | CH₃C(O)— | |
| 84. | 6 | —CH₂C≡CCH₂CH₃ | H | C₆H₅C(O)— | |
| 85. | 4 | —CH(CH₃)—C₆H₅ | H | —CH(cyclopentyl)CH₂— | |
| 86. | 5 | —C₆H₄—OH (p) | C₄H₉ | C₅H₁₁ | |
| 87. | 6 | C₈H₁₇ | H | C₂H₅ | |
| 88. | 7 | —(CH₂)₂C₆H₅ | C₃H₇ | C₇H₁₅ | |
| 89. | 8 | (cyclopentyl) | H | CH₃ | |

EXAMPLES 90 TO 101

Following the procedure of Example 3 and Example 1 except replacing the 4-carboxybutyltriphenylphosphonium bromide with the compound shown in Column I, replacing tosyl chloride in Example 3 Part B with the compound shown in Column II of Table II set out below and replacing methylhydroxylamine (in Example 1 Part M) with the compound shown in Column III, the product shown in Column IV is obtained (wherein A is —CH=CH—).

TABLE II

| | Column I | Column II | Column III | | Column IV |
|---|---|---|---|---|---|
| | $Br^-(C_6H_5)_3P^+$—$(CH_2)_m$—COOH | $R^2SH$ | $HN(R)$—$OR^1$ | | structure with bicyclic epoxide bearing $CH_2$—CH=CH—$(CH_2)_m$—C(O)—N(R)—$OR^1$ and $CH_2$—S—$R^2$ |
| Ex. No. | m | $R^2$ | R | $R^1$ | m as in Column I; $R^2$ as in Column II; R, $R^1$ as in Column III |
| 90. | 3 | $C_2H_5$ | H | H | |
| 91. | 4 | $C_6H_5$ | H | $C_4H_9$ | |
| 92. | 4 | —$CH_2C_6H_5$ | $C_3H_7$ | $C_6H_5$ | |
| 93. | 6 | | H | $C_6H_5CH_2$ | |
| 94. | 1 | —cyclohexyl | H | cyclohexyl | |
| 95. | 4 | —$CH_2$—CH=CH—$CH_3$ | $C_2H_5$ | $CH_3$C(=O)— | |
| 96. | 3 | —$CH_2C{\equiv}CCH_2CH_3$ | H | $C_6H_5$C(=O)— | |
| 97. | 4 | p-$CH_3$—$C_6H_4$—CH— | H | cyclopentyl-$CH_2$— | |
| 98. | 5 | p-HO—$C_6H_4$— | $C_4H_9$ | | |
| 99. | 6 | $C_8H_{17}$ | H | $C_2H_5$ | |
| 100. | 7 | —$(CH_2)_2C_6H_5$ | $C_3H_7$ | H | |
| 101. | 8 | cyclopentyl | H | H | |

EXAMPLES 102 TO 113

Following the procedure of Example 2 and Example 1 wherein Y is to be O or Example 3 wherein Y is to be S except replacing the 4-carboxybutyl triphenylphosphonium bromide with the compound shown in Column I, replacing hexylmesylate in Example 1 Part G or tosyl chloride in Example 3 with the compound shown in Column II of Table III set out below and replacing methylhydroxylamine in Example 1 Part M with the compound shown in Column III, the product shown in Column IV is obtained (wherein A is —(CH$_2$)$_2$—).

TABLE III

| Ex. No. | Column I<br>Br$^-$(C$_6$H$_5$)$_3$P$^+$—(CH$_2$)$_m$—COOH<br>m | Column II<br>R$^2$Br or R$^2$SH<br>YR$^2$<br>OR$^2$ or SR$^2$ | Column III<br>HN—OR$^1$<br>R<br>R    R$^1$ |
|---|---|---|---|
| 102. | 3 | —SC$_2$H$_5$ | H    H |
| 103. | 10 | —SC$_6$H$_5$S | H    C$_4$H$_9$ |
| 104. | 4 | —O—CH$_2$C$_6$H$_5$ | C$_3$H$_7$    C$_6$H$_5$ |
| 105. | 3 | —S—⬡ | H    C$_6$H$_5$CH$_2$ |
| 106. | 1 | —S—CH$_2$—⬡ | H    ⬡ |
| 107. | 4 | —O—CH$_2$—CH=CH—CH$_3$ | C$_2$H$_5$    CH$_3$C(=O) |
| 108. | 3 | —S—CH$_2$C≡CCH$_2$CH$_3$ | H    C$_6$H$_5$C(=O) |
| 109. | 9 | —S—CH(CH$_3$)—⬡ | H    ⬠—CH$_2$— |
| 110. | 5 | —O—⬡—OH | C$_4$H$_9$    C$_2$H$_5$ |
| 111. | 6 | —S—C$_8$H$_{17}$ | H    C$_2$H$_5$ |
| 112. | 7 | —O—(CH$_2$)$_2$C$_6$H$_5$ | C$_3$H$_7$    C$_3$H$_7$ |
| 113. | 8 | —S—⬠ | H    H |

Column IV

[norbornane]—CH$_2$—CH=CH—(CH$_2$)$_m$—C(=O)—N(R)—OR$^1$ ; CH$_2$—Y—R$^2$

| Ex. No. | m | —OR$^2$ or —SR$^2$ | R    R$^1$ |
|---|---|---|---|
| 102. | as in Column I | as in Column II | as in Column III |
| 103. | | | |
| 104. | | | |
| 105. | | | |
| 106. | | | |
| 107. | | | |
| 108. | | | |
| 109. | | | |
| 110. | | | |
| 111. | | | |
| 112. | | | |
| 113. | | | |

It will also be appreciated that the carboxybutyl triphenylphosphonium bromide of the structure

Br$^-$(C$_6$H$_5$)$_3$P$^+$—CH$_2$—CH$_2$—CH$_2$COOH employed in forming the upper side chain in the aforementioned examples may be replaced by

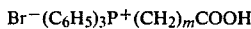

wherein $(CH_2)_m$ is defined hereinbefore, to form compounds of the invention wherein the upper side chain is of the structure

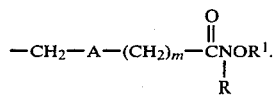

What is claimed is:

1. A compound of the structure

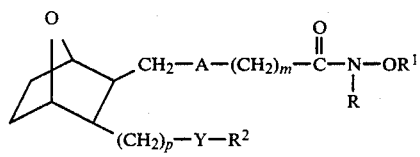

including all stereoisomers thereof, wherein A is —CH=CH— or —$(CH_2)_2$—; m is 1 to 10; R is H or lower alkyl; $R^1$ is H, lower alkyl, aryl, aralkyl, cycloalkyl, alkanoyl or aroyl; p is 1 to 5; Y is O or

wherein q is 0, 1 or 2; and $R^2$ is lower alkyl, aryl, arylalkyl, cycloalkyl, cycloalkylalkyl, lower alkenyl containing 2 to 12 carbons or lower alkynyl containing 2 to 12 carbons, provided that when $R^1$ is H, Y is $S(O)_q$, or a pharmaceutically acceptable salt thereof, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl or alkylcycloalkyl;

aryl alone or as part of another group contains 6 to 10 carbons in the ring portion and is unsubstituted or is substituted with 1 or 2 lower alkyl groups, 1 or 2 halogens, 1 or 2 hydroxy groups and/or 1 or 2 lower alkoxy groups; and cycloalkyl alone or as part of another group contains 3 to 12 carbons and is unsubstituted or is substituted with 1 or 2 halogens, 1 or 2 lower alkyl grups and/or 1 or 2 lower alkoxy groups.

2. The compound as defined in claim 1 wherein A is —CH=CH.

3. The compound as defined in claim 1 wherein A is —$(CH_2)_2$—.

4. The compound as defined in claim 1 wherein p is 1.

5. The compound as defined in claim 1 wherein m is 1 or 3.

6. The compound as defined in claim 1 wherein Y is O.

7. The compound as defined in claim 1 wherein Y is S.

8. The compound as defined in claim 6 wherein A is $CH_2$—$CH_2$ or CH=CH, m is 1 or 3, X is O, $R^1$ is H and R is lower alkyl, p is 1, Y is S and $R^2$ is lower alkyl, phenyl or benzyl.

9. The compound as defined in claim 1 wherein $R^2$ is butyl, pentyl, hexyl or heptyl including all isomers thereof.

10. The compound as defined in claim 1 [1R-[1α,2β(5Z),3β,4α]]-7-[3-[(hexyloxy)methyl]-7-oxabicyclo[2.2.1]hept-2-yl]-N-hydroxy-N,2,2-trimethylheptenamide.

11. A composition for inhibiting allergic conditions in a mammalian species, comprising an effective amount of a compound as defined in claim 1 or a pharmaceutically acceptable salt thereof, and a pharmaceutically acceptable carrier thereof.

12. A method of inhibiting $\Delta^5$-lipoxygenase which comprises administering to the circulatory system of a mammalian host an effective amount of a compound as defined in claim 1 or a pharmaceutically acceptable salt thereof.

13. The method as defined in claim 12 wherein said compound is administered in an amount within the range of from about 1 to about 100 mg/kg.

14. A method for treating asthma in a mammalian species in need of such treatment, which comprises administering to a mammalian host an effective amount of a compound of the structure

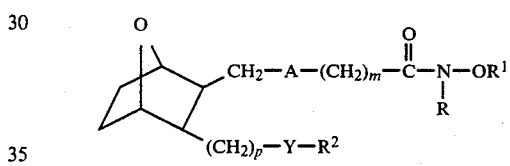

including all stereoisomers thereof, wherein A is —CH=CH— or —$(CH_2)_2$—; m is 1 to 10; R is H or lower alkyl; $R^1$ is H, lower alkyl, aryl, aralkyl, cycloalkyl, alkanoyl or aroyl; p is 1 to 5; Y is O or

wherein q is 0, 1 or 2; and $R^2$ is lower alkyl, aryl, arylalkyl, cycloalkyl, cycloalkylalkyl, lower alkenyl containing 2 to 12 carbons or lower alkynyl containing 2 to 12 carbons, or a pharmaceutically acceptable salt thereof, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl or alkylcycloalkyl;

aryl alone or as part of another group contains 6 to 10 carbons in the ring portion and is unsubstituted or is substituted with 1 or 2 lower alkyl groups, 1 or 2 halogens, 1 or 2 hydroxy groups and/or 1 or 2 lower alkoxy groups; and cycloalkyl alone or as part of another group contains 3 to 12 carbons and is unsubstituted or is substituted with 1 or 2 halogens, 1 or 2 lower alkyl groups and/or 1 or 2 lower alkoxy groups.

15. A method of inhibiting or reducing inflammation, which comprises administering to a mammalian host an effective amount of a compound of the structure

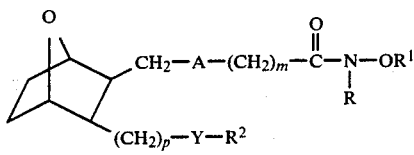

including all stereoisomers thereof, wherein A is —CH=CH— or —(CH$_2$)$_2$—; m is 1 to 10; R is H or lower alkyl; R$^1$ is H, lower alkyl, aryl, aralkyl, cycloalkyl, alkanoyl or aroyl; p is 1 to 5; Y is O or

wherein q is 0, 1 or 2; and R$^2$ is lower alkyl, aryl, arylalkyl, cycloalkyl, cycloalkylalkyl, lower alkenyl containing 2 to 12 carbons or lower alkynyl containing 2 to 12 carbons, or a pharmaceutically acceptable salt thereof, wherein lower alkyl or alkyl alone or as part of another group contains 1 to 12 carbons and is unsubstituted or is substituted with halo, CF$_3$, alkoxy, aryl, alkyl-aryl, haloaryl, cycloalkyl or alkylcycloalkyl;

aryl alone or as part of another group contains 6 to 10 carbons in the ring portion and is unsubstituted or is substituted with 1 or 2 lower alkyl groups, 1 or 2 halogens, 1 or 2 hydroxy groups and/or 1 or 2 lower alkoxy groups; and cycloalkyl alone or as part of another group contains 3 to 12 carbons and is unsubstituted or is substituted with 1 or 2 halogens, 1 or 2 lower alkyl groups and/or 1 or 2 lower alkoxy groups.

16. A method of inhibiting psoriasis, which comprises administering to a mammalian host an effective amount of a compound of the structure

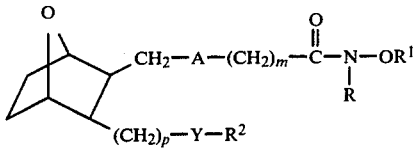

including all stereoisomers thereof, wherein A is —CH=CH— or —(CH$_2$)$_2$—; m is 1 to 10; R is H or lower alkyl; R$^1$ is H, lower alkyl, aryl, aralkyl, cycloalkyl, alkanoyl or aroyl; p is 1 to 5; Y is O or

wherein q is 0, 1 or 2; and R$^2$ is lower alkyl, aryl, arylalkyl, cycloalkyl, cycloalkylalkyl, lower alkenyl containing 2 to 12 carbons or lower alkynyl containing 2 to 12 carbons, or a pharmaceutically acceptable salt thereof, wherein lower alkyl or alkyl alone or as part of another group contains 1 to 12 carbons and is unsubstituted or is substituted with halo, CF$_3$, alkoxy, aryl, alkyl-aryl, haloaryl, cycloalkyl or alkylcycloalkyl;

aryl alone or as part of another group contains 6 to 10 carbons in the ring portion and is unsubstituted or is substituted with 1 or 2 lower alkyl groups, 1 or 2 halogens, 1 or 2 hydroxy groups and/or 1 or 2 lower alkoxy groups; and cycloalkyl alone or as part of another group contains 3 to 12 carbons and is unsubstituted or is substituted with 1 or 2 halogens, 1 or 2 lower alkyl groups and/or 1 or 2 lower alkoxy groups.

\* \* \* \* \*